US006755828B2

(12) United States Patent
Shevtsov et al.

(10) Patent No.: US 6,755,828 B2
(45) Date of Patent: Jun. 29, 2004

(54) DEVICE FOR EXTERNAL TRANSPEDICULAR SPINAL FIXATION, TECHNIQUE OF ITS USE

(75) Inventors: Vladimir Ivanovich Shevtsov, Kurgan (RU); Alexander Timofeevich Khoudiaev, Kurgan (RU); Pavel Ivanovich Kovalenko, Kurgan (RU)

(73) Assignee: Russian Ilizarov Scientific Center (RU)

( * ) Notice: Subject to any disclaimer, the term of this patent is extended or adjusted under 35 U.S.C. 154(b) by 0 days.

(21) Appl. No.: 10/241,735

(22) Filed: Sep. 12, 2002

(65) Prior Publication Data

US 2003/0065328 A1 Apr. 3, 2003

Related U.S. Application Data

(63) Continuation of application No. PCT/RU00/00036, filed on Feb. 3, 2000.

(30) Foreign Application Priority Data

Feb. 3, 2000 (RU) ............................. PCT/RU00/00036

(51) Int. Cl.[7] .......................... A61B 17/66; A61B 17/88
(52) U.S. Cl. .............................. 606/54; 606/61; 606/57; 606/59
(58) Field of Search ........................... 606/54, 55, 56, 606/57, 58, 59, 61

(56) References Cited

U.S. PATENT DOCUMENTS

| 5,498,262 A | * | 3/1996 | Bryan ........................ 606/60 |
| 5,681,312 A | * | 10/1997 | Yuan et al. .................. 606/61 |
| 5,947,965 A | * | 9/1999 | Bryan ........................ 606/69 |
| 6,302,883 B1 | * | 10/2001 | Bono ........................ 606/70 |

* cited by examiner

Primary Examiner—Cary E. O'Connor
Assistant Examiner—Candice C. Melson
(74) Attorney, Agent, or Firm—Rothwell, Figg, Ernst & Manbeck, PC (57) ABSTRACT

The invention relates to medicine, in particular to spinal surgery and is used for curing spinal diseases and injuries in specialized departments of vertebrology and neurosurgery. The inventive device includes not more than nine fixing units. Each unit bears two fixing elements fastened to it which are embodied in the form of a threaded stem, the working ends of which are implanted in roots of vertebra arches angularly at 35–45° to the sagittal plane of the vertebra. The fixing units are connected to each other in groups of three with the aid of threaded ties, thereby forming support units. Two of the units are side units and one is intermediate unit. The intermediate unit is connected to the side support units so that it can move with the aid of the connecting hinge junctions. Dosed displacement is performed by moving distraction nuts. Displacement of noninvolved vertebrae is carried out until a normal correction of the spinal column occurs and ostial and ostial-fibrotic blocks are built up in the area of discotomy of vertebrae.

16 Claims, 10 Drawing Sheets

DEVICE FOR EXTERNAL TRANSPEDICULAR SPINAL FIXATION, TECHNIQUE OF ITS USE

CROSS-REFERENCE TO RELATED APPLICATION

The present application is a continuation of PCT/RU00/00036, filed Feb. 3, 2000.

FIELD OF THE INVENTION

The invention refers to the field of medicine, specifically to that of orthopaedics and, and exactly to spinal surgery, and is used for treatment of diseases and injuries of the spine in specialized departments of vertebrology and neurosurgery.

DESCRIPTION OF THE PRIOR ART

An implanted device for spinal fixation is known, comprising a screw for spongy bone bearing an improved saddle-shaped configuration fixed in a place with a nut and comprising a simple and effective locking mechanism having some pins, each of them contacts with an upper half-saddle and a nut to prevent rotation of the latter with respect to the rest of the configuration. The implanted system also comprises rods, rigidly caught by the saddle-shaped configuration and a sublaminar wire, where the rod/wire interface is protected with a wire tread (U.S. Pat. No. 5,030,220. IPC$^5$ A 61 F 5/04, A 61 F 5/00).

A rod screw is known as well as a device for correction and fixation with that kind of a screw, in which the rod screw has a threaded part and a spherical segment or a head, on the latter a packing is set with a connecting element to set a rod, and the connecting element and the packing are connected with each other in such a way, that the distance between its end and the connecting element can be changed (International Application N WO 91/06254. IPC$^5$ A 61 B 17/60).

A device for spinal treatment is known, comprising junctions of vertebral fixation with curved needles, connected by straight screws with each other, and two units, which are connected with central plates, on which straight needles are fastened with the help of plates held down and screws (Author Certificate/A.c./1537237, A 2, USSR. IPC$^5$ A 61 B 17/60). In the known device the central plates are made as a semicircle, supplied with holes and cut-outs. Moreover, vertebral fixation is performed using curved needles inserted into the spinous process and straight needles inserted into vertebral body.

A technique of modeling closed insertion of fixators into the vertebral body is known, comprising its stabilization by insertion of wire-markers in the spinous process in the middle sagittal plane, after that, displacing from it at first in the cranial and then in the lateral direction the fixators are inserted into safe zones from backward forward at an angle to the sagittal plane, and their direction is marked on a template, which is then used during insertion of the fixators (U.S. Pat. No. 2,093,901, C1, RF).

A technique for insertion of a threaded rod in vertebral body is known as well as a device for this implementation (U.S. Pat. No. 2,051,633, C1, RF). The essence of the invention is in pre-insertion of a guiding axial wire, a guide with a central longitudinal hole, a protective tube, with the help of which protection of soft tissues is made, direction and depth of the threaded rod implantation are controlled, for this a device for osteosynthesis is used provided with a rotation mechanism as a case, including a ratchet with a lock, a quadrangular jack with a ball fixator on one end and a handle with circular recesses, set on the opposite end perpendicular to the case.

A compression-distraction device is known, including rings and arches, wire fixators, tie screws, spherical hinges, fixing elements, in which each pair of the tie screws is connected by the spherical hinge, and the rings and arches are set at a regulated distance from the plane of the hinge arrangement (A.c.374076, USSR).

A device for fixation and correction of the spine is known, comprising threaded rods and a base, provided with lever ties (U.S. Pat. No. 2,019,148, C1, RF). There are longitudinal threaded bars in the known device, each of them is made being consisted of three parts, connected with each other by hinges and provided with rod holders as a cylinder with a fixing element and a slot, thereby the parts provide multi-planar transport of the threaded rods.

A device for treatment of spinal curvatures is known, in which two support junctions are connected with each other by a reposition junction, using threaded rods of distractors (A. c. 1781872, A 1, USSR). The reposition junction has two cross-pieces, connected with each other by hinges and with the help of rods respectively with plates. A shackle with a stud is set on one of the threaded rods; a flexible traction, fixed to the spine in the apex of the curvature, is attached in the transverse hole.

A device for treatment of scoliosis is known, comprising staples with holes and a slot, attached to them support elements and fixation elements, in which one of the staple ends is deviated along the plane to its convex side, a fixing plate with L-reversed section is arranged on the staple with the possibility of its transport along the slot and fixation; a slider is on one of its wall, it is sunk into the staple slot and becomes an axle, in the top of which, in its turn, a threaded pole is made, and a slot, parallel with the staple plane, is made in the other wall of the fixing plate, a tractor is set by hinges on the axle of the fixing plate, its threaded end is attached to the deviated end of the staple through a face support, bone rods and clips are in the slots of the fixing plates with the possibility of transport and fixation, the latter consist of two arched plates with tenons, connected by a tie bolt at their base, and the staples are connected with each other with the possibility of their interlocation change and fixation by use of hinge bars (U.S. Pat. No. 2,086,202, C 1, RF).

A device and a technique for spinal extrafocal osteosynthesis are known, the device comprises threaded rods, support elements, screw tractions and fixing elements, the support elements in the device are made as arched plates with curvature radius 140±10 mm and longitudinal slots, in which the threaded rods are fastened perpendicular to the plane of the support plate, the threaded rods are to be inserted in vertebral bodies, free movements are made within 30°-range with respect to the support plate at the expense of compensatory washers, the support elements have free movements within 60°-range and are connected with each other by posts with the compensatory washers and the longitudinal screw tractions in two parallel planes. In the technique of spine extrafocal osteosynthesis by transpedicular insertion of the threaded rods in bodies of some adjacent intact vertebrae with attachment to the external support transpedicular fixation is supplemented by fixation of spinous process, in an involved vertebra the rods are inserted directly in the body, omitting the arch, and two adjacent vertebrae are fixed by a single support plate, for example, the involved vertebra and the one below, thereby creating repositional moment of forces at the level of the most involved spinal motor segment (Application N 96113284/14, A, RF, Publ. 10.27.1998.).

ESSF device is known, which has transverse beams, made integral and provided with apertures to set ball hinges with lock screws (Weber B. G., Magenl F. The external fixator. AO/ASIF—Thread Rod System Spine—Fixator. Berlin: Springer-Verlag, 1985.—P. 298–300). The transverse beams are connected with each other by threaded rods and the ball hinges. All the threaded rods have antirotational thread. In the device Schanz screws are used, which are connected by the transverse beams, using screw clamps. Slots, made in the transverse beams, give the possibility to change transverse distance of the Schanz screws.

However, the design of the device mentioned above doesn't allow to correct spinal deformities and exactly scoliosis of Grade III-IV, because setting the ball hinges in the transverse beam apertures limits its use versatility due to absence of the possibility of setting ball hinges, oriented to the deformity apex.

A device is known for infusion of medication solutions into bone and soft tissues, comprising a case with a tubular needle, a union for solution feeding in and a mandrin with a cone plug and a handle, set with the possibility of rotation around the axis, a longitudinal groove and as a perpendicular to it narrowing capillary gap are made on its mandrin cone plug, the mandrin with the needle form a throttling valve, the flow section of which is the same as the cross-section of the longitudinal groove (A. c. 858839, USSR. IPC$^3$ A 61 M 1/00).

A device is known for intraosseous injections, comprising a handle with a longitudinal canal and a slot, a separable needle, set on the handle, a mandrin with a slider, set with the possibility of transport in the handle and needle canals, and a fixator of the mandrin position, in which a handle is provided with two stops at its ends, the fixator is set on the stop of the handle working end and the shape of the handle working end conforms with the shape of the mandrin working end (A. c. 914063, USSR. IPC$^4$ A 61 M 1/00).

However, the design of the device mentioned above is intended for independent use and it is not provided for its use in combination with the vertebral fixation element.

A clamp is known, comprising two handles, connected by hinges, with rings and a rack-and-pinion lock and working jaws, where the working jaws are made with cheek-pieces and slotted bottom, moreover, the closed slots form a round hole (A. c. 850064, USSR. IPC$^3$ A 61 B 17/18).

However, design of the working jaws doesn't allow to use the known clamp for insertion of the fastening end of the vertebral fixation element through soft tissues to vertebral body.

A device for scoliosis treatment is known, comprising supports, set in parallel and interconnected, on which elements of vertebral fixation are fastened, in which each support is made as a plate, provided with connecting shanks, the latter are fastened in posts, set with the possibility of transport in slots of schwellers, moreover, each preceding support is connected with each following one with the possibility of transport (Certificate 1797 for utility model, RF. IPC$^6$ A 61 B 17/60).

A correcting device for the spine is known, comprising a unit of vertebral fixation, which is made from a support as two bars, connected with each other by a central support element and at the ends, having lateral support elements. In the longitudinal slots of the bars clamps with vertebral fixators are set (U.S. Pat. No. 2,128,021, C1 RF. IPC$^6$ A 61 B 17/66, 17/70).

However, the design of the known devices hasn't sufficient stiffness due to the fixation junction, having a large number of built-up elements.

SUMMARY OF THE INVENTION

It is an object of the present invention to design a device for external transpedicular fixation of the spine for correction of its deformities and injuries, an instrument for insertion of the vertebral fixation element, and a technique of their use for treating deformities and injuries of the spine.

The object is achieved due the fact that in the device for external transpedicular fixation of the spine, comprising not less than 6 fixation junctions connected with each other through ties into support units connected through threaded rods capable to produce mutual transport and indirect effect on intact vertebrae, into each of said vertebrae the working ends of two vertebral fixation elements are inserted while the fastening ends of said fixation elements are secured with clamps in each said fixation junction provided with holes, there are not more than 9 fixation junctions fastened by ties in threes as three support units, two of them are outer and one is intermediate, each of them is connected with the other with the possibility of spatial transport with the help of not more than 6 distraction rods, the ends of each out of three distraction rods are indirectly connected with one of the fixation junctions of the outer support units and correspondingly with the fixation junctions of the intermediate support unit, moreover, each of the fixation junctions is made as a figure plate having a transverse axis of symmetry and provided with symmetric through longitudinal slots located between a central bulge and ends made as a prism while the central bulge and the prism-shaped ends are provided with connecting holes and fastening elements, moreover, to each of the fixation junctions not more than two elements of vertebral fixation are attached by clamps, said elements are made as half pins, each of them has a working end made cone-shaped and provided with screw-shaped thread limited by a stopper and a fastening end on which a flattening is made supplied with a through hole, the axis of the latter is perpendicular to longitudinal axis of the half pin.

Preferably, each of the fixation junctions is made as a figure plate shaped as an isosceles trapezium and, respectively, a transverse axis of symmetry of the plate provided with symmetric through connecting holes, the axis of each of the latter is perpendicular to the transverse axis of symmetry and the connecting holes are made in the middle and at the ends of each plate, moreover, each of them is provided with two pairs of through mounting slots made at angle 35–40° on both sides from the transverse axis of symmetry of the plate and in said slots, in one out of the pair, one element of vertebral fixation is fastened made as a half pin; the outer support units are connected with the intermediate one by connecting hinge junctions, each of them is assembled from interconnected posts and each of the said posts is provided with distraction rods.

Such an implementation of the fixation junctions of the mentioned device allows to increase fixation rigidity of intact vertebrae using the elements of their fixation, fastening ends of which are oriented at angle 35–40° with respect to the spinal longitudinal axis, and to regulate an adjustment of the fixing site of the fastening ends of the elements of vertebral fixation in view of applied distraction forces.

Simultaneously, the object to achieve infusion of medication solutions in the bodies of vertebrae is solved during their fixation in the process of treatment due to the fact that each half pin is provided with a longitudinal slot made all over the half pin length, and in the slot an injection needle is fixed in which a cannula provided with a plug is set from the direction of the fastening end of the half pin.

To provide complete correction of spinal deformity both in trauma and Grade 3–4 scoliosis cases it is preferable to embody each of the connecting hinge junctions as a ball head and a hollow sphere, both having cylindrical bulges with holes, while the ball head is set on the truncated and opposite to the cylindrical bulge side in a hollow sphere the inner surface of which is covered with antifriction coating; distraction rods are set in the holes of the cylindrical bulges; the truncated part is equal to ⅓ of the hollow sphere and the angle of the truncated part in projection is 90°; moreover, the ball head is provided with recesses and the hollow sphere with a hole, the axis of which is perpendicular to the axis of the hole of the cylindrical bulge in which a lock is set.

Moreover, each of the connecting hinge junctions can be made as a distraction rod provided with a ball head on one of the ends, the head is set in a sleeve connected with a ball pivot made on one of the ends of the second distraction rod.

In a variant of the invention implementation the device can be provided with a microschweller, on one plane of which a longitudinal slot is made and at least two mounting holes on each side from it, the microschweller is connected with the outer support units through two posts and threaded rods, and it is connected with the intermediate support unit through a lug with a threaded shank with the possibility of transport in the sagittal plane.

The embodiment of the device with such kind of traction provides an additional effect during correction of a lateral spinal deformity and increases the design rigidity.

To prevent slipping of the vertebral fixation element during its fastening on the fixation junction each of its fixation clamps is preferably made as an angular post embodied as a cylinder with threaded surface and connected at an angle with a prismatic head having a cylindrical deepening into its inner surface from the side of the cylinder, the axis of the deepening is perpendicular to the axis of the cylinder on which conical and spherical washers can be set.

According to the invention a technique of usage of the device for external transpedicular fixation for correction of spinal deformities and injuries has been developed, including percutaneous insertion of the vertebral fixation elements into vertebral bodies and fastening of the elements in the fixation junctions for subsequent application of distraction forces in the damaged area of the spine in which a laminectomy and discotomy of cranially and caudally located spinal discs at the deformity apex are performed, autografts are inserted into the cavity of each disc, the intact vertebrae above and below are fixed using the elements of vertebral fixation, which are inserted into the centre of each arch at the angle 30–45° to the sagittal plane which passes through the axis of each vertebra, after that the spine is gradually corrected to biomecanically normal position by graduated transport of the support units using connecting elements, and, respectively, of the intact vertebrae located above and below the area of surgical intervention.

BRIEF DESCRIPTION OF THE DRAWINGS

The patented invention will be made clear by the following detailed description of each specific case of implementation with references to the accompanying drawings and diagrams.

DESCRIPTION OF PREFERRED IMPLEMENTATION OF THE INVENTION

Figure 1:
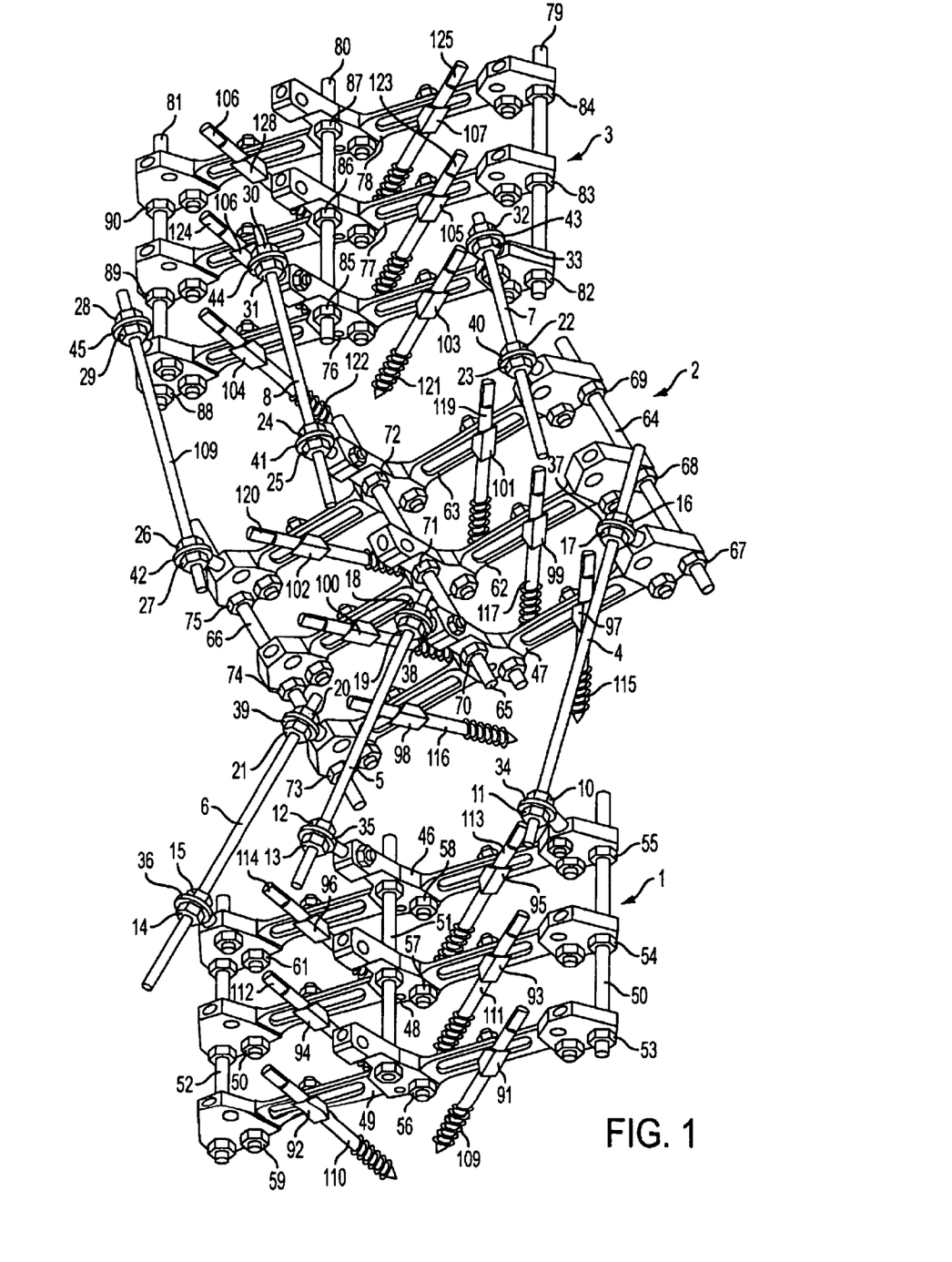
FIG. 1 is a configuration of the device for external transpedicular fixation of the spine according to the invention, general view.

Refer now to FIG. 1 of the accompanying drawings, which illustrates the device for external transpedicular fixation of the spine as a whole.

The device comprises not more than three support units 1, 2, 3. In this configuration the support units 1 and 3 are outer, and the support unit 2 between them is intermediate. The support units 1, 2, 3 are connected with each other with the possibility of relative transport using distraction threaded rods 4, 5, 6, 7, 8, 9, distraction nuts 10 and 11, 12 and 13, 14 and 15, 16 and 17, 18 and 19, 20 and 21, 22 and 23, 24 and 25, 26 and 27, 28 and 29, 30 and 31, 32 and 33, and, respectively, lugs 34, 35, 36, 37, 38, 39, 40, 41, 42, 43, 44, 45 with threaded shanks. The lugs 34, 35, 36 with the threaded shanks are set with the possibility of their fastening in the holes of the fixation junction 46 of the outer support unit 1, and lugs 37, 38, 39 with their threaded shanks are set and fastened in the holes of the fixation junction 47 of the intermediate support unit 2.

The support unit 1 is assembled from three fixation junctions 46, 48, 49, which are connected with each other by threaded ties 50, 51, 52 and, respectively, by pairs of fastening nuts 53, 54, 55, located on the threaded tie 50, by pairs of fastening nuts 56, 57, 58, located on the threaded tie 51, and by pairs of fastening nuts 59, 60, 61, located on the threaded tie 52.

The support unit 2 is assembled from three fixation junctions 47, 62, 63, which are connected with each other by threaded ties 64, 65, 66 and, respectively, by pairs of fastening nuts 67, 68, 69, located on the threaded tie 64, by pairs of fastening nuts 70, 71, 72, located on the threaded tie 65, and by pairs of fastening nuts 73, 74, 75, located on the threaded tie 66.

The lugs 34, 35, 36 and 37, 38, 39 are located on threaded rods 4, 5, 6 and can be transported by pairs distraction nuts, namely: 10 and 11, 12 and 13, 14 and 15, 16 and 17, 18 and 19, 20 and 21.

The lugs 40, 41, 42 are located on threaded rods 7, 8, 9 and can be transported by pairs of the distraction nuts, namely: 22 and 23, 24 and 25, 26 and 27. Moreover, the lugs 43, 44, 45 are also located on threaded rods 7, 8, 9 and can be transported by pairs of the distraction nuts, namely: 28 and 29, 30 and 31, 32 and 33. The threaded shanks of lugs 43, 44, 45 are set in the holes of fixation junction 76 of outer support unit 3 with the possibility of transport.

The support unit 3 is assembled from three fixation junctions 76, 77, 78, which are connected with each other by threaded ties 79, 80, 81 and, respectively, by pairs of fastening nuts 82, 83, 84, located on the threaded tie 79, by pairs of fastening nuts 85, 86, 87, located on the threaded tie 80, and by pairs of fastening nuts 88, 89, 90, located on the threaded tie 81.

Pairs of vertebral fixation elements, namely: 109, 110, 111, 112, 113, 114, 115, 116, 117, 118, 119, 120, 121, 122, 123, 124, 125, 126, are fastened, respectively, on each fixation junction 46, 47, 48, 49, 62, 63, 76, 77, 78, using the clamps, namely: 91, 92, 93, 94, 95, 96, 97, 98, 99, 100, 101, 102, 103, 104, 105, 106, 107, 108.

Figure 2:
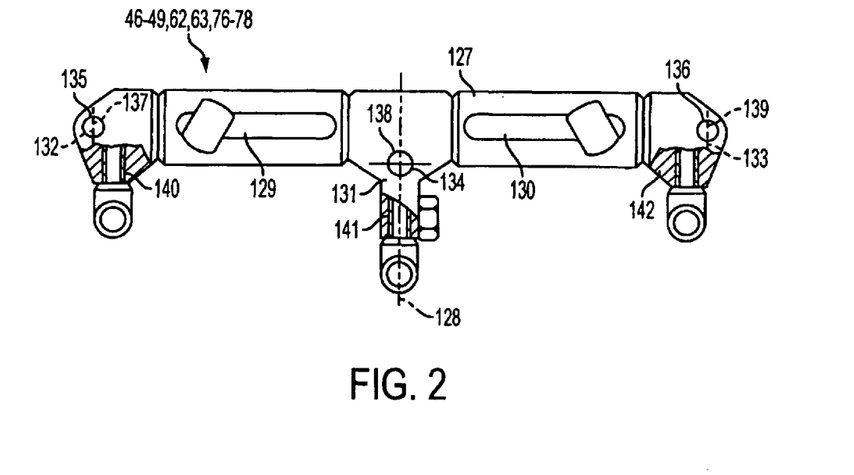
FIG. 2 is a fixation junction according to the present invention.

Each of the fixation junctions 46, 47, 48, 49, 62, 63, 76, 77, 78 is made as symmetrical figure plate 127 with a transverse axis of symmetry 128 (FIG. 2). Symmetrical through longitudinal slots 129 and 130 are made in the plate, they are located between the central bulge 131 and ends 132, 133 of the figure plate 127. Connecting holes 134, 135, 136 are made in the central bulge 131 and in each of ends 132, 133. Each of the holes has the central axis 137, 138, 139, located as a perpendicular to the transverse axis of symmetry 128. Besides, the central bulge 131 and in each of ends 132, 133 of the figure plate have mounting holes 140, 141, 142, the central axes of which are perpendicular to central axes 137, 138, 139 of the connecting holes 134, 135, 136.

Figure 3:
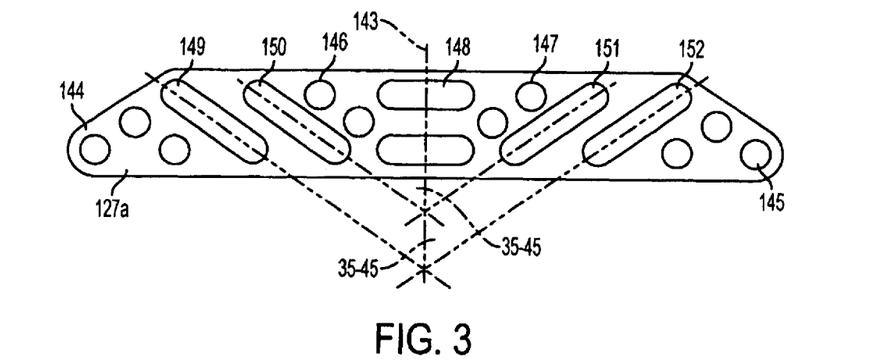
FIG. 3 is a possible variant of the fixation junction implementation.

The figure plate 127 can be embodied as an isosceles trapezium, in a variant of the fixation junction implementation with the purpose to increase fixation rigidity of intact vertebrae and to control the position of the attached fastening ends of the vertebral fixation elements, in view of applied distraction forces (FIG. 3). The trapezium figure plate has a transverse axis of symmetry 143. Connecting holes 144 and 145 are made on the ends of the figure plate 127a, and connecting holes 146, 147, 148 are made in the central part of the plate. Each of connecting holes 144, 145, 146, 147, 148 has the central axis, perpendicular to the plane of the figure plate 127a. Longidudinal slots 149, 150, 151, 152 are made at the angle 35–45° to the transverse axis of symmetry and they are located in couples, namely: 149, 150 and 151, 152, on two sides from it and, respectively, between the connecting holes, namely: 144, 146 and 145, 147.

The elements of vertebral fixation 109–126 are attached by one to each of longidudinal slots 129, 130 (FIG. 1) of each fixation junction 46, 47, 48, 49, 62, 63, 76, 77, 78, and the elements of vertebral fixation 109–126 are attached to each of longidudinal slots 149 or 150 and 151 or 152 (FIG. 4) of each of fixation junctions 153–161. Each of the elements of vertebral fixation is correspondingly attached by clamps 91–108.

Moreover, the fixation junctions 153–161 (FIG. 4) made as a figure plate shaped as an isosceles trapezium are connected with each other forming three groups, and namely: 153, 154, 155, and 156, 157, 158 and 159, 160, 161 by threaded ties 50, 51, 52, and 64, 65, 66 and 79, 80, 81, respectively, set in corresponding connecting holes, thereby forming three support units. One of the support units is intermediate and two others are outer ones. The plates 155, 156 and 158, 159 are interconnected by distraction rods 162, 163, 164, 165, 166, 167, 168, 169, 170, 171, 172, 173 and connecting hinge junctions 174, 175, 176, and 177, 178, 179. Each of the connecting hinge junctions 174, 175, 176, 177, 178, 179 is made from two interconnected posts with the possibility of rotation through a connecting element. The axis of rotation of each connecting hinge junction 174, 175, 176, 177, 178, 179 is parallel to the plane of each of the plates 155, 156, 158, 159.

The elements of vertebral fixation 109–126 (FIGS. 1, 4), made as half pins, are attached in couples to each of plates 153–161. Each of the half pins has a working end 180 (FIG. 5), being cone-shaped and provided with a screw-like thread, a stopper 181, and a fastening end 182, on which a flattening 183 is made, provided with a through hole 184. The axis of the hole 184 is perpendicular to the longitudinal axis of the half pin.

Each half pin can be provided with a longitudinal slot 185, made all over the half pin length (FIGS. 6, 7) for the purpose to infuse medication solutions into the bodies of vertebrae during their fixation in the process of treatment. In the longitudinal slot 185 an injection needle 186 is fastened, in which a cannula 187, provided with a plug 188, is set on the side of the fastening end 182.

Figure 8:
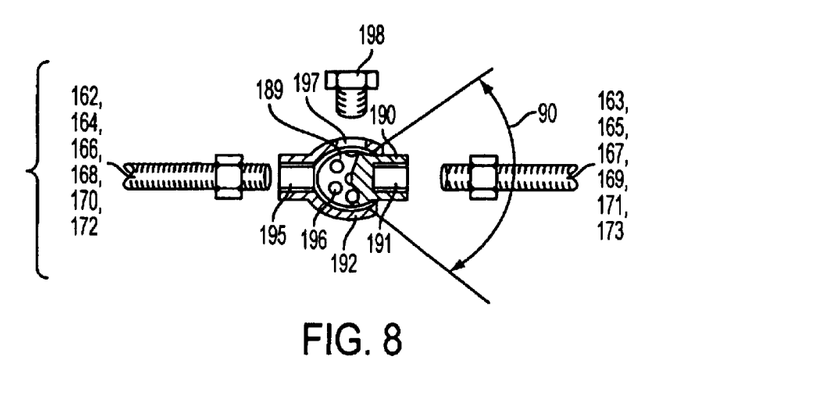
FIG. 8 shows a possible variant of implementation of a connecting ball hinge, according to the invention.

In the variant of the invention implementation in order to obtain a complete correction of spinal deformity each of connecting hinge junctions 174, 175, 176, 177, 178, 179 can be made as ball head 189 (FIG. 8), having a cylindrical bulge 190 with a hole 191. The ball head 189 is set into a hollow sphere 192 from its truncated part, the inner surface of which is covered with antifriction coating. The truncated part 193 of the sphere 192 is equal to ⅓ of the volume, and the angle in projection of the truncated part 193 is 90°, that is equal to the maximal angle of scoliotic spinal deformity. Besides, the hollow sphere 192 is provided with a cylindrical bulge 194 and a hole 195. Distraction rods 163, 165, 167, 169, 171, 173, and 162, 164, 166, 168, 170, 172, respectively, are set in holes 191 and 195 of each connecting hinge junction with the possibility of transport. The ball head 189 is provided with recesses 196, and the hollow sphere 192 has a hole 197, in which a lock 198 is set.

Figure 9:
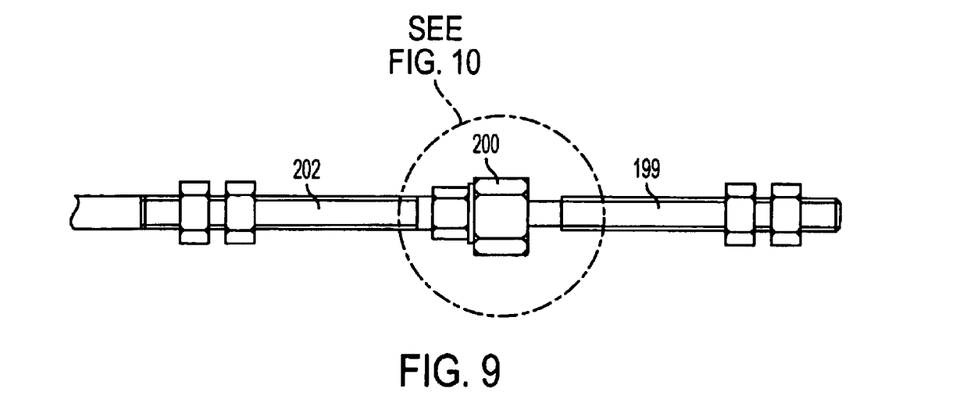
FIG. 9 is a possible variant of implementation of a connecting ball hinge, according to the invention.
Figure 10:
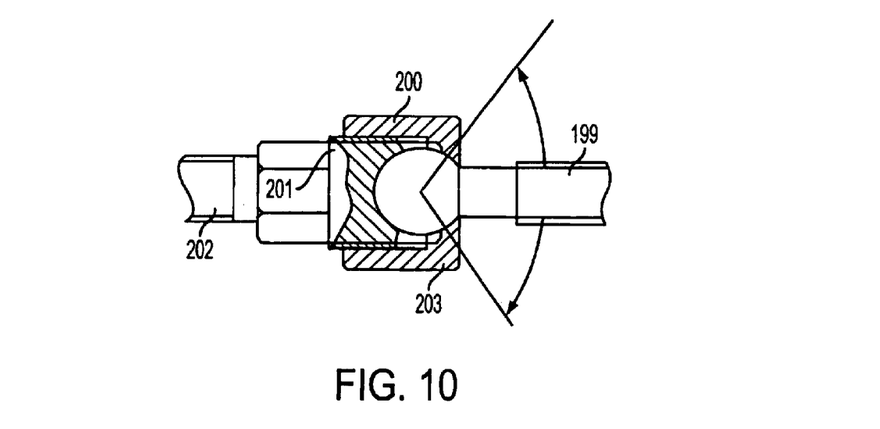
FIG. 10 is an additional picture of the same connecting ball hinge.

Moreover, each of connecting hinge junctions 174, 175, 176, 177, 178, 179 can be made as a distraction rod 199 (FIGS. 9, 10), provided on one of the ends with a ball head which can be set in a sleeve 200. The latter is connected with a pivot 201, made on one of the ends of the other distraction rod 202. In this case projection of the angle drilling is 90°. The proposed variant of the connecting hinge junctions is easier in manufacturing.

Figure 11:
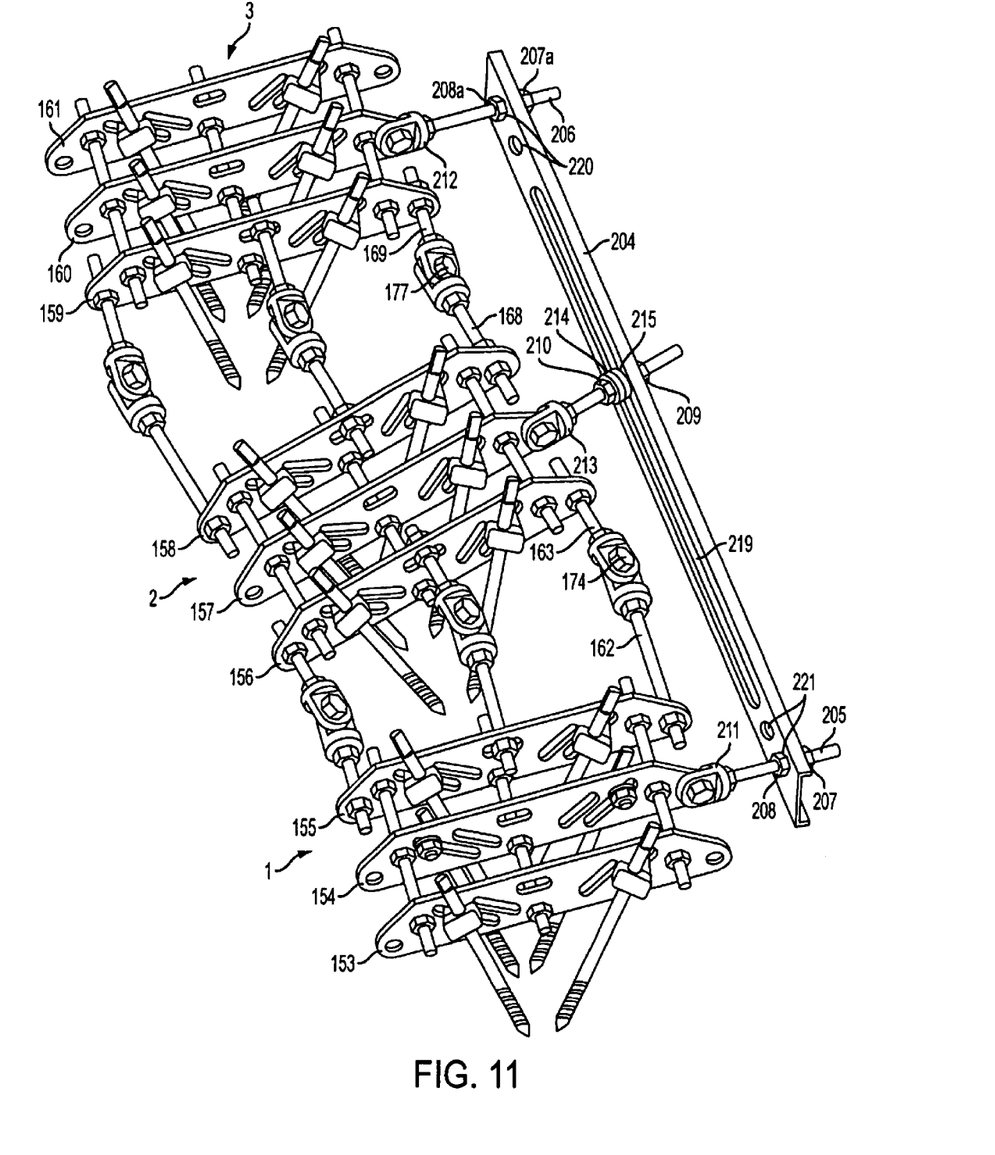
FIG. 11 is a possible variant of the configuration of the device for external transpedicular fixation of the spine using a microschweller, according to the invention.
Figure 12:
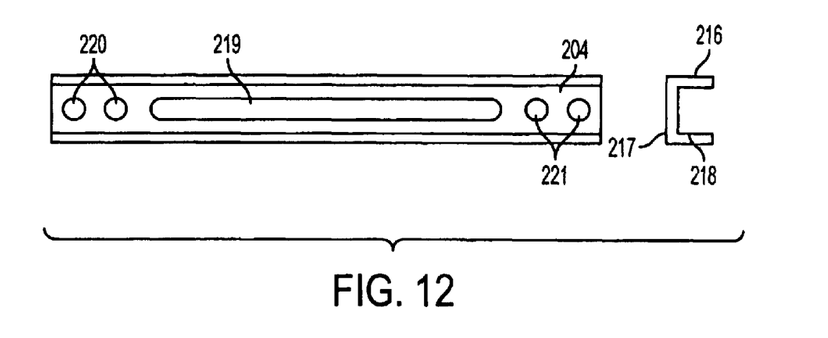
FIG. 12 is an implementation of the microschweller, according to the invention, the same as in FIG. 11.
Figure 13:
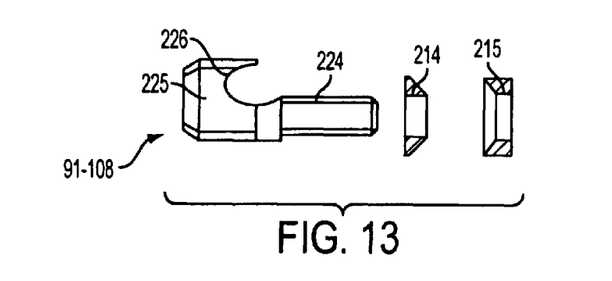
FIG. 13 shows a clamp for fastening the element of vertebral fixation to the fixation junction, according to the invention.

In a variant of the invention implementation the device can be provided with a microschweller 204 in order to achieve an additional effect during correction of lateral spinal deformity and to increase the construction rigidity (FIG. 11). The microschweller 204 is connected through posts 211, 212, set on the fixation junctions 154, 160 of outer support units 1 and 3, respectively, with the possibility of transport using threaded rods 205, 206 and two pairs of load-bearing nuts 207, 208, and 209, 210, respectively. Moreover, the fixation junction 157 of the intermediate support unit 2 is connected with the microschweller 204 by a connecting element 213, a pair of load-bearing nuts 209, 210 and two pairs of conical 214 and spherical 215 washers, respectively (FIG. 12). The microschweller has three planes 216, 217, 218, two of them, namely: 216, 218, are parallel and attached to the ends of the third plane 217 at the angle 90°. A closed slot 219 is longitudinally made on the plane 217, and on both sides from it at least two through holes 220, 221 are made, the axis of which is a perpendicular to plane 217. In this case the connecting element 213 (FIG. 13) is made as a lug with threaded shank 222 and a through hole 223, and the axis of the lug is a perpendicular to the axis of the threaded shank 222.

To prevent slipping of each element of vertebral fixation 109–126 fixed with the help of the clamps 91–108, each clamp (FIGS. 1, 4) is made as an angular post, formed by a cylinder with threaded surface 224 and connected at the right angle with a prismatic head 225, on the inner surface of which a cylindrical deepening 226 with cut file teeth is made from the side of the cylinder. In this case conical 214 and spherical 215 washers are set on the threaded surface of the cylinder 224 of each of the clamps.

Figure 15:
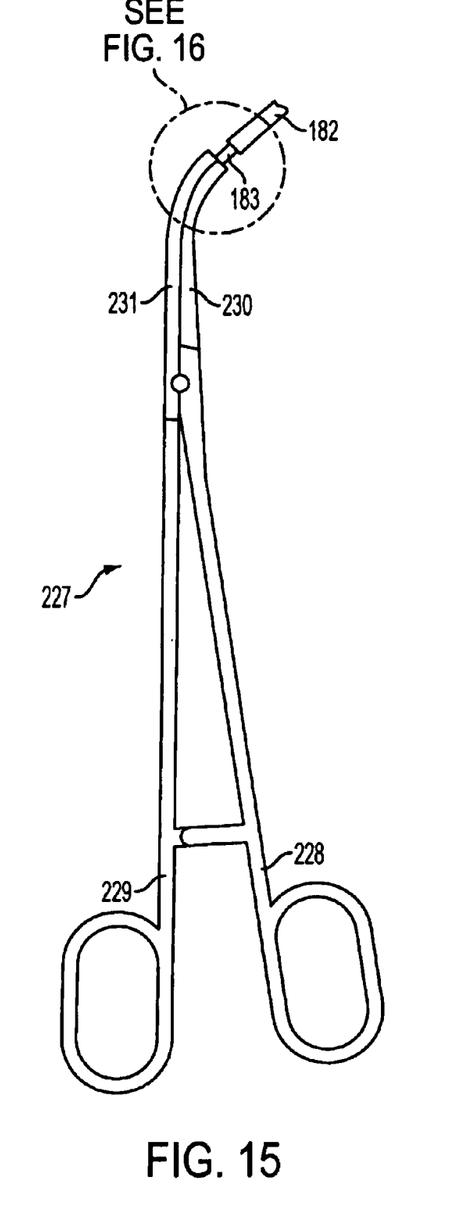
FIG. 15 is a surgical clamp for insertion of the element for vertebral fixation, according to the invention.

In order to reduce damage to the soft tissues, adjacent to the spine, a surgical clamp 227 is used during insertion of the vertebral fixation elements 109–126 (FIG. 15). Handles 228, 229 of the surgical clamp have jaws 230, 231. The jaw 231 has a cylindrical boss 232, which is coaxial to hole 233, made in the jaw 230 so that the diameter of the cylindrical boss 232 should not exceed the diameter of the through hole 184 (FIG. 5) made in the flattening 183 of the fastening end 182 of the vertebral fixation element.

The device for external transpedicular fixation of the spine and the technique of its use can be used as follows.

Figure 17:
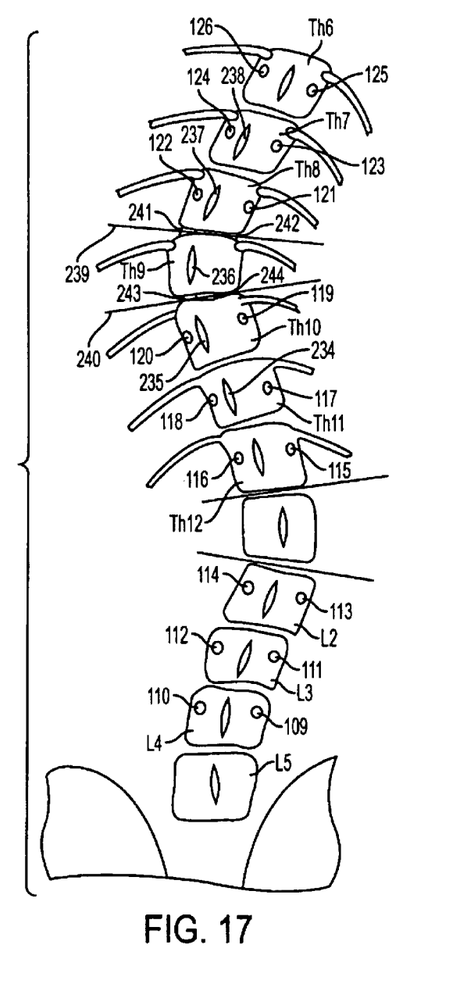
FIG. 17 is a diagram of the deformed spine, according to the invention.

The examination done before surgical treatment determines the indications and scope of the surgery. In case of Grade III-IV scoliosis the skin, being antiseptically treated twice previously, is cut along the line of the spinous processes of the vertebrae $Th_7$, $Th_8$, $Th_9$, $Th_{10}$, $Th_{11}$, under endotracheal anesthesia (FIG. 17). Aponeuroses are cut on both sides from the the spinous processes 234, 235, 236, 237, 238. The longest muscles of the back are separated with a raspatory, and hemostasis is performed with a hot physiologic salt solution. The laminectomy of $Th_9$ vertebra is performed with partial resection of vertebral arches $Th_8$ and $Th_{10}$.

The discotomy of the discs on both sides from the spinal cord is performed using a chisel: 239 cranial vertebrae $Th_8$–$Th_9$ and 240 caudal vertebrae $Th_9$–$Th_{10}$, which are at the apex of the deformity. Then autografts 241, 242, 243 and 244 respectively, prepared from the spinous process 236 and arches of $Th_8$, $Th_9$, $Th_{10}$ vertebrae, are inserted into the cavities of discs 239 and 240.

Figure 14:
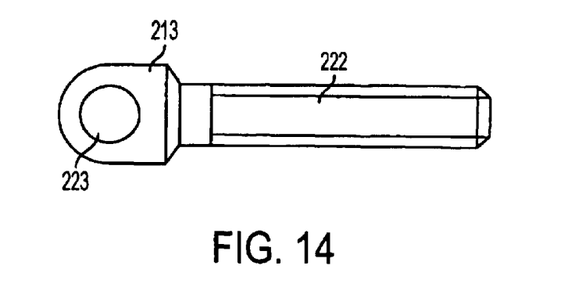
FIG. 14 is a post made as a lug with a threaded shank.

After that transpedicular fixation of the intact vertebrae is performed. Insertion of the vertebral fixation elements in their bodies is made through arch roots; the elements are made as half pins 109–126 (FIG. 14).

The insertion of the half pin 125 into the intact vertebra $Th_6$ is illustrated.

Figure 4:
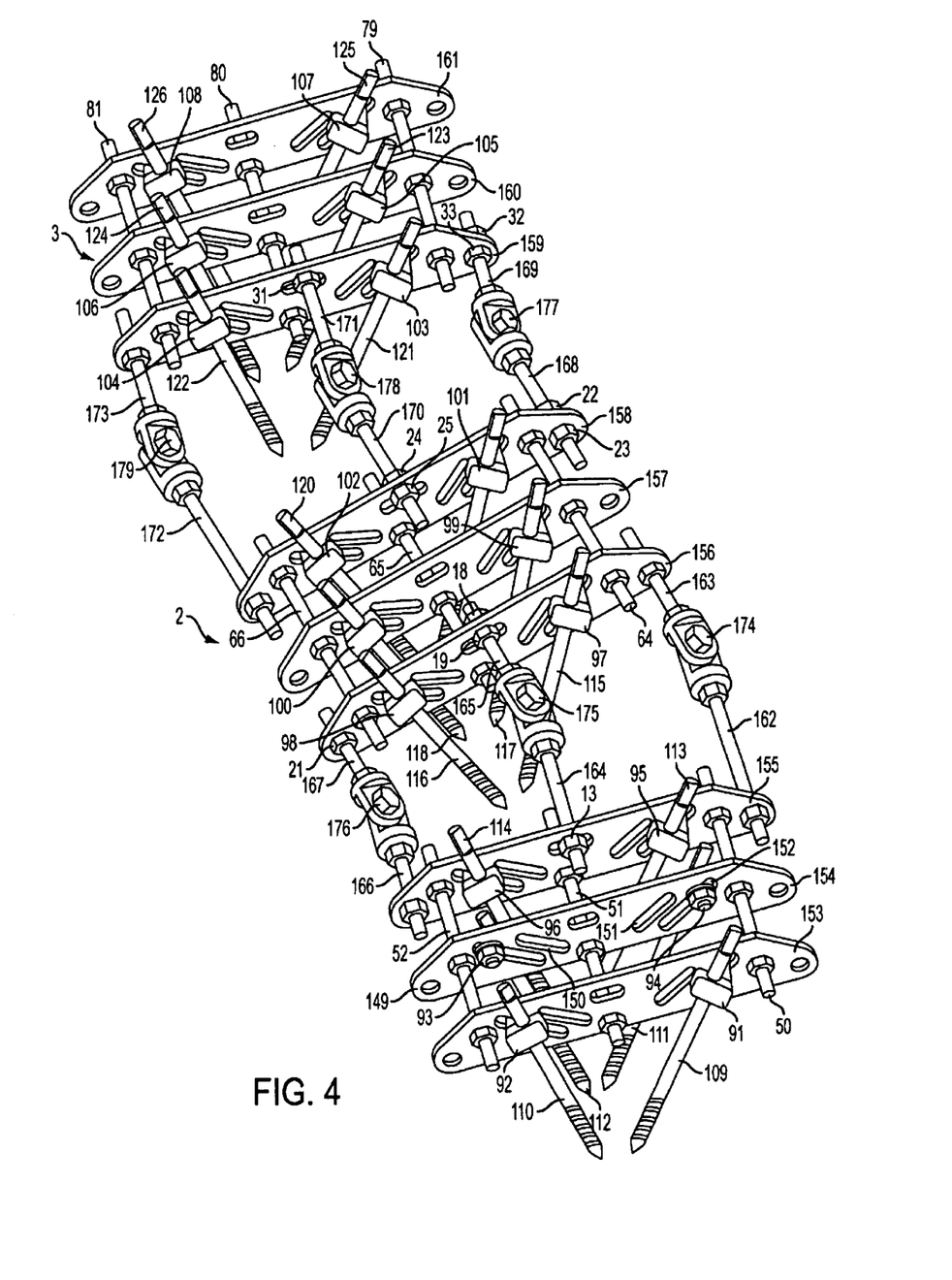
FIG. 4 illustrates a possible variant of the configuration of the device for external transpedicular fixation of the spine.
Figure 5:
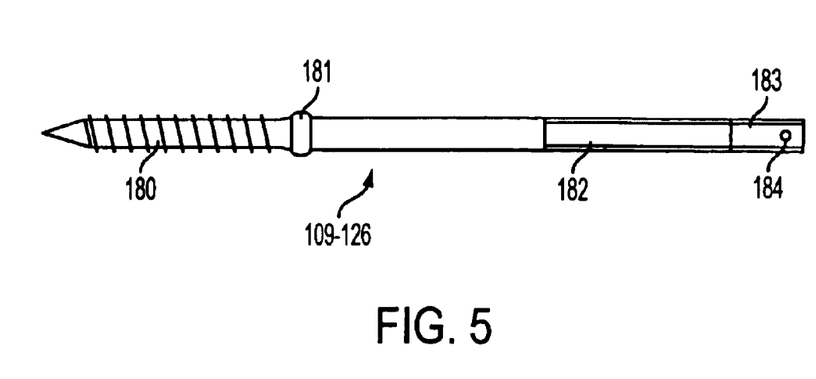
FIG. 5 shows an element for vertebral fixation, made as a half pin, according to the invention.
Figure 16:
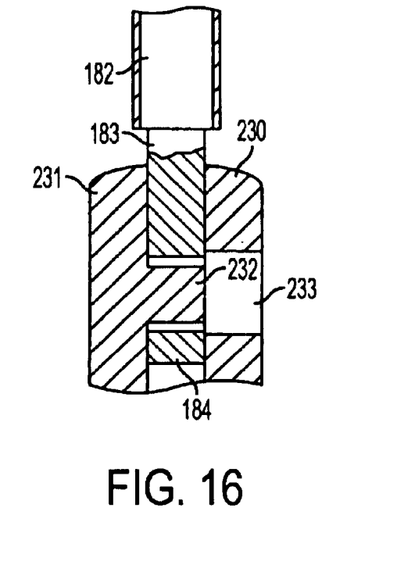
FIG. 16 is a diagram of the surgical clamp jaws the with a fixed flattened end of the vertebral fixation element.
Figure 19:
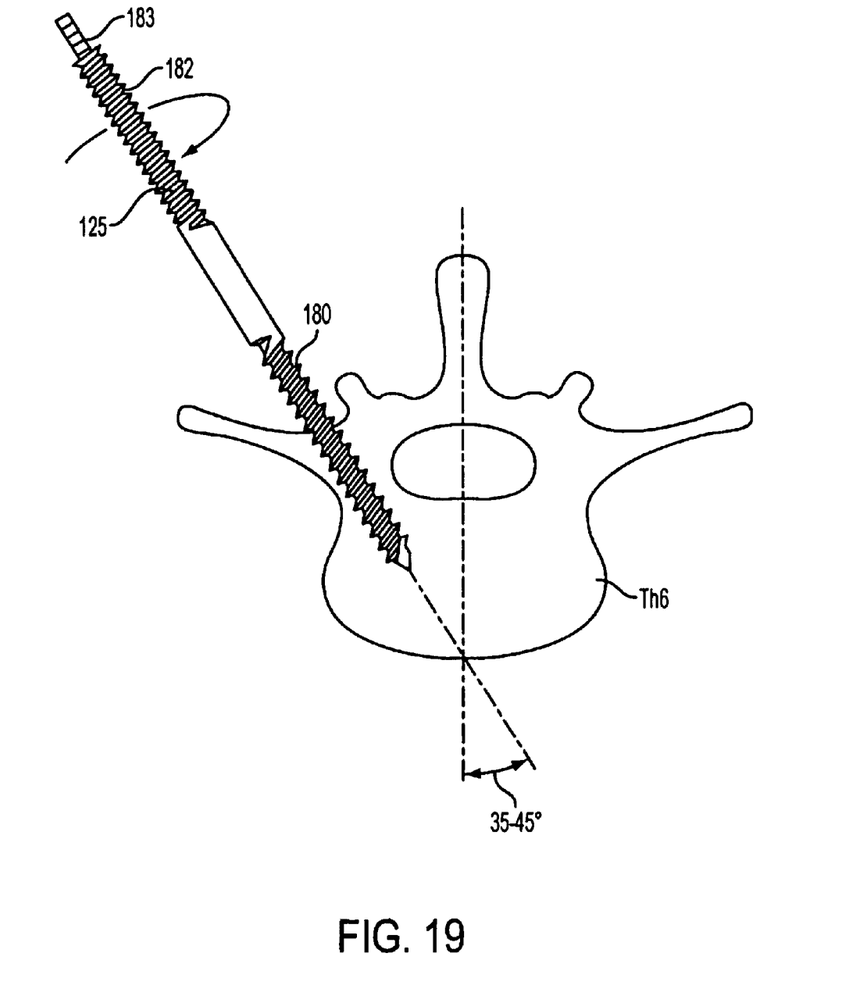
FIG. 19 shows the element of vertebral fixation, inserted into the vertebral body.

The surgical clamp 227 is used for insertion of the half pins 125 and 126 through soft tissues (FIG. 15). An additional incision of about 1 cm is made in soft tissues in the projection of the pedicle of the arch of $Th_6$ intact vertebra. A canal is formed from the additional incision in the soft tissues towards the incision along the line of the spinous processes, using jaws 231, 230 of the surgical clamp. After that the boss 232 (FIG. 16) of the jaw 231 of the handle 229 is inserted into the hole 184 of the flattening 183 of the fastening end 182 of the half pin 125 (FIGS. 1, 4). The flattening 183 is grasped with the handles 229, 228 and it is clamped. The fastening end 182 is pulled through the canal formed in soft tissues. The working end 180 (FIG. 19) of the half pin 125 is set in the centre of the arch pedicle of the intact vertebra $Th_6$, being oriented at angle 35–45° to the sagittal plane 245, and after that it is screwed on into the arch of the intact vertebra $Th_6$.

The half pin 126 (FIGS. 1, 4) is inserted similarly, as well as the half pins 123, 124, respectively, into the intact vertebra $Th_7$, the half pins 121, 122 into the intact vertebra $Th_8$, the half pins 119, 120 into the intact vertebra $Th_{10}$, the half pins 117, 118 into the intact vertebra $Th_{11}$, the half pins 115, 116 into the intact vertebra $Th_{12}$, the half pins 113, 114 into the intact vertebra $L_2$, the half pins 111, 112 into the intact vertebra $L_3$, the half pins 109, 110 into the intact vertebra $L_4$. Layer-by-layer suturing of the incision along the line of the spinous processes of the intact vertebrae $Th_6$, $Th_7$, $Th_8$, $Th_{10}$, $Th_{11}$, $Th_{12}$, $L_2$, $L_3$, $L_4$ is performed upon insertion of the half pins 109–126 into these vertebrae. The fastening ends of the inserted half pins 109–126 (FIGS. 1, 4) are secured using conical 214 and spherical 215 washers (FIG. 14) and clamps 91–108, made as angular posts and which are set in each of the longitudinal through slots 129, 130 (FIG. 2) of each fixation junction 78, 77, 76, 63, 62, 47, 46, 48, 49, made as a figure plate. The fastening ends of the half pins 125, 126 (FIG. 1) are fixed, respectively, with the clamps 107, 108 in the fixation junction 78. The fastening ends of the half pins 123, 124 are fixed, respectively, with clamps 105, 106 in the fixation junction 77. The fastening ends of the half pins 121, 122 are fixed, respectively, with the clamps 103, 104 in fixation junction 76. The fastening ends of the half pins 119, 120 are fixed, respectively, with the clamps 101, 102 in the fixation junction 63. The fastening ends of the half pins 117, 118 are fixed, respectively, with the clamps 99, 100 in the fixation junction 47. The fastening ends of the half pins 113, 114 are fixed, respectively, with the clamps 95, 96 in the fixation junction 46. The fastening ends of the half pins 111, 112 are fixed, respectively, with the 93, 94 in the fixation junction 48. The fastening ends of the half pins 109, 110 are fixed, respectively, with the 91, 92 in the fixation junction 49.

The fixation junctions 76, 77, 78 (FIG. 1) made as figure plates are connected using threaded ties 79, 80, 81, set in the connecting holes and secured with pairs of fastening nuts: 82, 83, 84, 85, 86, 87, 88, 89, 90, thereby forming the outer support unit 3. The fixation junctions 47, 62, 63 are connected using threaded ties 64, 65, 66 secured with pairs of fastening nuts: 67, 68, 69, 70, 71, 72, 73, 74, 75, thereby forming the intermediate support unit 2. And the fixation junctions 46, 48, 49 are connected using threaded ties 50, 51, 52 and matching pairs of fastening nuts: 53, 50, 55, 56, 57, 58, 59, 60, 61, thereby forming the other outer support unit 1. The lugs 34, 35, 36, 40, 41, 42, 43, 44, 45 are connected through threaded shanks secured in the mounting holes of the matching fixation junctions, and namely: 76 of the outer support unit 3, 63 and 47—those of the intermediate support unit 2, and 46—that of the outer support unit 1. The lugs 43 and 40, 44 and 41, 45 and 42, 37 and 34, 38 and 35, 39 and 36 are connected with the possibility of transport using the threaded rods 7, 8, 9, 6, 5, 4, respectively, and pairs of distraction nuts: 32 and 33, 22 and 23, 30 and 31, 24 and 25, 28 and 29, 26 and 27, 20 and 21, 15 and 14, 18 and 19, 12 and 13, 16 and 17, 10 and 11, respectively.

Figure 18:
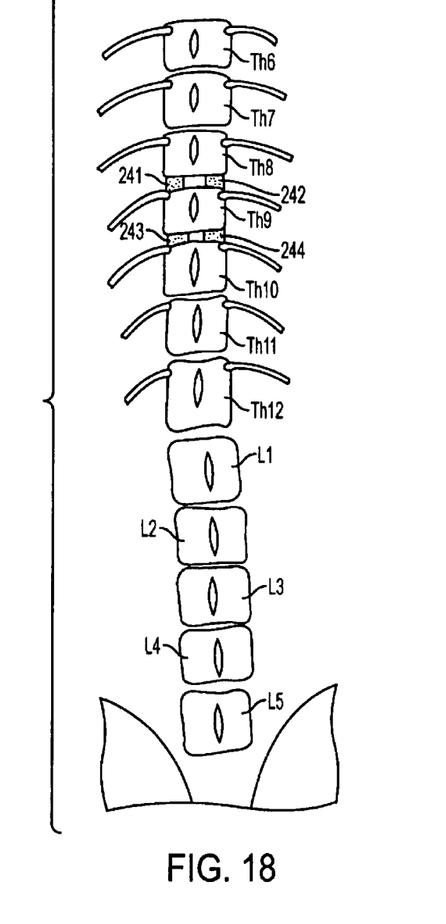
FIG. 18 is the same spine as in FIG. 17 after correction of the spinal deformity, using the device for external transpedicular fixation.

Graduated transport of the support units, the outer unit 3 (FIG. 1) and the intermediate one 2, is performed along the concave side of the spine. By untwisting the distraction nuts 32 and 23, located on the threaded rod 7, the lugs 43 and 40 are transported. By twisting pairs of distraction nuts 25 and 24, 30 and 31 the lugs 41 and 44, respectively, are transported in the opposite direction releasing the latter for the period of graduated transport of the lugs 43 and 40, which indirectly transfer the applied distraction forces to the fixation elements 121, 122, 123, 125, 126 (FIGS. 1, 17) inserted in the intact vertebrae $Th_6$, $Th_7$, $Th_8$ and to the fixation elements 119, 120, 118, 117, 115, 116, inserted into the intact vertebrae $Th_{10}$, $Th_{11}$, $Th_{12}$, by their graduated transport in the cranial and caudal directions, respectively. After graduated transport of the lugs 43 and 40 (FIG. 1) the distraction nuts 33 and 22 are fastened on the threaded rod 7 and the distraction nuts 30 and 31, 24 and 25 on the threaded rod 8. Simultaneously, the distraction nuts 14 and 20 located on threaded rod 6 should be untwisted. Pairs of distraction nuts 12 and 13, 18 and 19, located on the threaded rod 5, are moved in the opposite directions from the lugs 35 and 38. After that by twisting the distraction nuts 12 and 21, through indirect effect of the lugs 36 and 39 in the outer 1 and the intermediate 2 support units, the fixation elements 110, 112, 114 transport the intact vertebrae $Th_{10}$, $Th_{11}$, $Th_{12}$ (FIG. 17) in the cranial direction and $L_2$, $L_3$, $L_4$ in the caudal direction. After graduated transport of the lugs 36 and 39 (FIG. 1) the distraction nuts 15, 21 on the threaded rod 6 and pairs of distraction nuts 12 and 13, 18 and 19 on the threaded rod 5 are fastened. The lugs 36, 35 of the support unit 1, the lugs 39, 38, 42, 41 of the support unit 2, and the lugs 45, 44 of the support unit 3 have the possibility of spatial rotation, thereby taking up a functionally favourable position relative to the distraction threaded rods 6, 5, 7, 8, respectively. The intact vertebrae $Th_6$, $Th_7$, $Th_8$ and $Th_{10}$, $Th_{11}$, $Th_{12}$, $L_2$, $L_3$, $L_4$, located above and below the area of surgical intervention, are moved with a set rate gradually as it has already been mentioned, and thus the spine is unbent (FIG. 18) using the system for external transpedicular fixation. The achieved alignment the spine is fixed up until an osseous or osseous-fibrous regeneration in the area of discotomies gets mature.

In a variant of the invention implementation each of the fixation junctions is made as a plate 127a(FIG. 3) shaped as an isosceles trapezium with a transverse axis of symmetry 143. The plate 127a has connecting holes 144, 146, 148, 147, 145 and through mounting slots 149, 150, 151, 152. The latter are located in pairs on both sides from the transverse axis of symmetry 143 of the plate and are made at an angle 35–45°. During assembling the device for external transpedicular fixation the elements of fixation 109, 110, 112, 113, 114, 115, 116, 117, 118, 119, 120, 121, 122, 123, 124, 125, 126 of intact vertebrae are inserted into their bodies similarly to the technique described above. The support units 1, 2, 3 are mounted from the fixation junctions, made as plates 153, 154, 155, 156, 157, 158, 159, 160, 161 (FIG. 4) shaped as an isosceles trapezium. The fastening ends of two vertebral fixation elements, namely: 109, 110, 111, 112, 113, 114, 115, 116, 117, 118, 119, 120, 121, 122, 123, 124, 125 and 126, respectively, are attached to each of the plates in the through mounting slots, using clamps 91 and 92, 93 and 94, 95 and 96, 97 and 98, 99 and 100, 101 and 102, 103 and 104, 105 and 106, 107 and 108, respectively. The outer support unit 1 is formed by connecting the plates 153, 154, 155 through threaded ties 50, 51 and 52, which are located in the connecting holes of the plates 153, 154 and 155, and fastened to the latter with pairs of nuts.

The intermediate support unit 2 is formed by connecting plates 156, 157, 158 through threaded ties 64, 65, 66, which are set in the connecting holes of the plates 156, 157, 158, and fastened to the latter with pairs of nuts. The outer support unit 3 is formed by connecting plates 159, 160, 161 through threaded ties 79, 80, 81, which are set in the connecting holes of the plates 159, 160, 161, and attached to the latter with pairs of nuts.

The outer support unit 1 is connected with the intermediate support unit 2 through three pairs of distraction rods 162 and 163, 164 and 165, 166 and 167. Each pair of the said rods is connected by a connecting hinge junction, namely: 174, 175, 176. The ends of distraction rods 162 and 163, 164 and 165, 166 and 167 of each pair are set in the connecting holes of the respective plates 155 and 156 with the possibility of transport. The axis of each connecting hinge junction is parallel to the sagittal plane.

The intermediate support unit 2 is connected with the outer support unit 3 through three pairs of distraction rods 168 and 169, 170 and 171, 172 and 173. Each pair is connected by the connecting hinge junction, namely: 177, 178, 179. The ends of distraction rods 168 and 169, 170 and 171, 172 and 173 of each pair are set in the connecting holes of the respective plates 158 and 159 with the possibility of transport. The axis of each connecting hinge junction is parallel to the sagittal plane. Distraction nuts 13, 12 (not shown) and 19, 18, respectively, on distraction rods 164 and 165, distraction nuts 25, 24 and 31, 30 (not shown) on distraction rods 170 and 171 are untwisted in the opposite directions from plates 155, 156 and 158, 159, respectively, to produce graduated transport of intact vertebrae. Besides, distraction nuts 52, 20 (not shown) on distraction rods 164 and 167 and distraction nuts 23, 32 on distraction rods 168 and 169 are untwisted. After that distraction nuts 21 and 15 (not shown) should be transported along distraction rods 166 and 167, and distraction nuts 22 and 33 along distraction rods 168, 169 to a graduated amount. Distraction nuts 13, 12 (not shown), 19, 18, 14, 15 (not shown), 21, 20 (not shown), 22, 23, 33, 32, 25, 24, 31, 30 (not shown) are fastened. Such graduated transport is performed periodically until a planned biomechanical axis correction of the spine is obtained.

In order to produce an additional effect on the spine during correction of severe deformity and to increase the design rigidity the fixation junctions 154, 160, respectively (FIG. 11), of the outer support units and the fixation junction 157 of the intermediate support unit 2 are connected to a microschweller 204 (FIGS. 11, 12). The latter has a plane 217, which is connected with planes 216 and 218 at right angles. Through holes 220, 221 and closed longitudinal slot 219 are made in plane 217.

The threaded shank 222 (FIG. 13) of connecting post 213, fastened with the help of load-bearing nuts 209, 210, is set in closed longitudinal slot 219 (FIG. 11), using conical 214 and spherical 215 washers. The lug of the post 213 is connected with a connecting hole of the fixation junction 157 (FIG. 11), using a through hole 223 and a bolt. One of the through holes on both sides from the closed longitudinal slot 219 bears threaded rods 205 and 206, respectively, fastened with two pairs of load-bearing nuts 207, 208 and 207a and 208a. The threaded rods are connected with posts 211 and 212, respectively, which are attached to the fixation junctions 154 and 160, respectively, with the help of bolts.

To obtain additional traction, the of load-bearing nuts 207, 208 and 207a, 208a on the threaded rods 205 and 206 are untwisted in different directions from the microschweller 204, and the load-bearing nut 209 on the threaded shank of the post lug 213 is untwisted as well. Then graduated turning of the load-bearing nut 210 is performed, and the required transport of the microschweller 204 in the transverse plane is performed. The load-bearing nuts 207, 208, 207a, 208a, 210 are fixed then. The graduated transport in the transverse plane should be repeated using the described technique.

Figure 6:
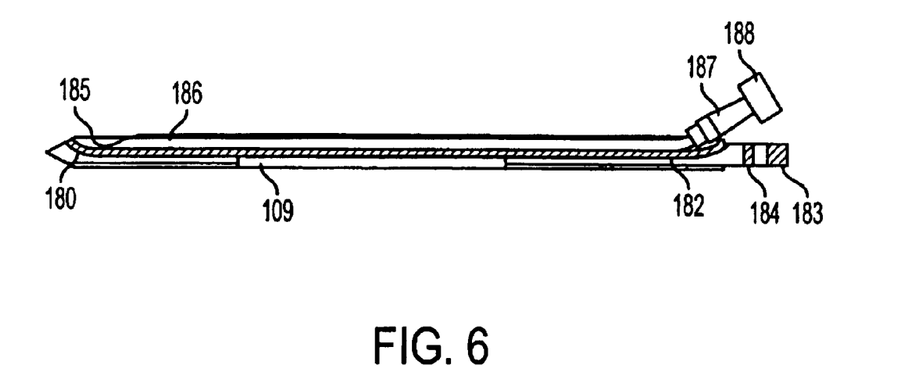
FIG. 6 illustrates a possible variant of implementation of the vertebral fixation element.
Figure 7:
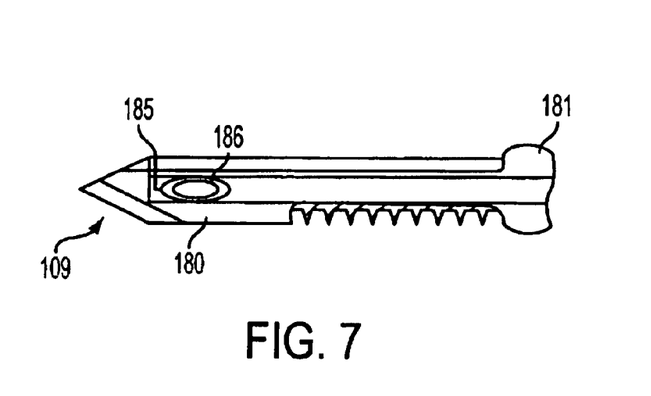
FIG. 7 is the same element for vertebral fixation as that in FIG. 6, top view.

To infuse medications in the bodies of vertebrae during their fixation in the process of treatment the elements of vertebral fixation 109, 110, 111, 112, 113, 114, 115, 116, 117, 118, 119, 120, 121, 122, 123, 124, 125, 126 are used, each of them is made as a half pin 109 (FIGS. 6, 7). A longitudinal slot 185 is made all over the length of the latter, where an injection needle 186 is fixed. The end of the injection needle 186 is located near the sharp working end 180 of the half pin 109, which it is provided with a cannula 187 and a plug 188 on the side of fastening end 182. Insertion and fastening of the half pin 109, provided with the injection needle 186, in the fixation junction is performed in the similar way, using the technique described above. Thus, in case of required prevention or treatment of inflammation the plug 188 should be removed from the cannula 187, a medication is infused by stream or by drops through the injection needle 186, fixed in the half pin 109, which is inserted in the body of the intact vertebra.

To achieve a complete correction of the spine deformities both for trauma and for scoliosis of Grade III-IV a multi-axial connecting hinge junction can be used in the assembly of the device for external transpedicular fixation for connection of the support units 1, 2, 3, thereby the ball head 189 in this junction (FIG. 8) which has a cylindrical bulge 190 is set in the hollow sphere 192. The cylindrical bulge 190 in this case is located on the side of truncated part comprising ⅓ of the hollow sphere, and a projection angle is equal to 90°, being the greatest angle of scoliotic deformity of the spine. The hollow sphere is provided with a cylindrical bulge 194 on the outer surface. Holes 191 and 195, respectively, are made in the cylindrical bulges 190 and 194. In each of the holes the distraction threaded rods 163, 165, 167, 169, 171, 173 and 162, 164, 166, 168, 170, 172 are set, respectively. Fixation of spatial position can be produced through recesses 196, made on each ball head 189, a hole 197 in each hollow sphere 192 and a lock 198, set in this hole. The inner surface of each hollow sphere 192 is covered with antifriction coating. From 2 to 6 the mentioned connecting hinge junctions can be used in the assembly of the device for external transpedicular fixation.

Moreover, each of the connecting hinge junctions can be made as a distraction rod 199 (FIGS. 9, 10) with a ball head is made on one of its ends. The head is located in a sleeve 200 with a bore angle 203 of 90°, equal to the greatest angle of the scoliotic deformity. The ball head of the distraction rod 199 is held in the sleeve 200 with the help of a pivot 201, which is made on the end of the distraction rod 202. The pivot 201 is connected with the sleeve 200 through thread. From 2 to 6 connecting hinge junctions can be used in the described design of the device for external transpedicular fixation.

INDUSTRIAL USABILITY

The patented invention is not limited by the variants of its implementation and use, described above, and includes other possible modifications within the applied claims.

The device for external transpedicular fixation of the spine proposed for patenting, having minimal nomenclature of parts included, allows to assemble constructions of the device, intended for treatment of the spine diseases of various etiology: acute and neglected dislocations, injuries, spondylolistheses, scolioses, kyphoses.

The proposed device provides simultaneous fixation of both anterior and posterior structures of the spine, thereby results in rigid fixation of vertebrae, high ability to control intact vertebrae position, provides rigidity of the device—spine system.

Moreover, a secure contact with the vertebrae allows application of strictly graduated distraction forces to the spine in any direction and at any stage of treatment.

What is claimed is:

1. A device for external transpedicular fixation of the spine, comprising at least six fixation junctions connected with each other by ties thereby forming support units (1, 2, 3), the said units are connected with each other by threaded rods (4, 5, 6, 7, 8, 9) with the possibility of relative transport and indirect effect on intact vertebrae ($Th_6$, $Th_7$, $Th_8$, $Th_{10}$, $Th_{11}$, $Th_{12}$, $L_2$, $L_3$, $L_4$) while into each of them the working ends of two vertebral fixation elements (109–126) are inserted whereas the fastening end of each of the elements is secured by clamps (91–108) to each of the fixation junctions provided with holes, characterized that said device has not more than nine fixation junctions (46, 47, 48, 49, 62, 63, 76, 77, 78) fastened by three through threaded ties (50, 51, 52, 64, 65, 66, 79, 80, 81) into three support units (1, 2, 3), two of them being outer ones (1, 3) and one being intermediate (2) while each of them is connected with the other through not more than six threaded rods (4, 5, 6, 7, 8, 9) with the possibility of spatial transport, and the ends of each of three threaded rods (4, 5, 6, 7, 8, 9) are indirectly connected with one of the fixation junctions (46, 78) of the outer support units (1, 3) and with the fixation junctions (47, 63) of the intermediate support unit (2) correspondingly, whereas each of the fixation junctions (46, 47, 48, 62, 63, 76, 77, 78) is made as a figure plate (127) which has a transverse axis of symmetry (128) and is provided with symmetrical through longitudinal slots (129, 130) located between a central bulge (131) and the ends made as a prism (132, 133) while the central bulge (131) and prism-like ends (132, 133) are provided with connecting holes (134, 135, 136) and fastening elements so that not more than two vertebral fixation elements (109–126) are attached to each of said fixation junctions (46, 47, 48, 49, 62, 63, 76, 77, 78) with clamps (91–108) and said vertebral fixation elements are made as half pins, each of them having a working end (180) made conical and provided with screw thread limited with an olive-shaped stopper (181) and a fastening end (182) with a flattening (183) provided with a through hole (184), the axis of which being perpendicular to the longitudinal axis of the half pin.

2. A device as claimed in claim 1, characterized that each of said half pins (109–126) is provided with a longitudinal slot (185) made all over the half pin length in which an injection needle (186) is fixed, and a cannula (187) provided with plug (188) is set on said needle from the side of the fastening end (182) of said half pin.

3. A device as claimed in claim 1, characterized that each of connecting hinge junctions (174–179) is made as a distraction rod (199) having a ball head on one of its ends and said ball head is set in a sleeve (200) connected with a pivot (201) made on one of the ends of the second distraction rod (202).

4. A device as claimed in claim 1, characterized that each of said clamps (91–108) is made as an angular post which is formed from a cylinder with threaded surface (224) connected at the right angle with a prismatic head (225) on the inner surface of which a cylindrical deepening (226) is made from the side of threaded surface of said cylinder (224) on which conical (214) and spherical (215) washers are set (224).

5. A device as claimed in claim 1, characterized that said the device is provided with a microschweller (204) on one of the planes of which a closed longitudinal slot (219) is made and at least two through holes (220, 221) on each side from the slot; moreover, said microschweller (204) is connected with said outer support units (1, 3) using posts (211, 212) and threaded rods (205, 206) while the intermediate support unit (2) is connected to it through a connecting element having a lug (213) with a threaded shank with the possibility of transport in the sagittal plane.

6. A device as claimed in claim 1, characterized that each of said fixation junctions (46, 47, 48, 49, 62, 63, 76, 77, 78) is made as a plate (143) shaped as isosceles trapezium (127a) having a transverse axis of symmetry and provided with symmetrical through connecting holes (144, 145, 146, 147, 148), so that the axis of each of the said connecting holes is perpendicular to the transverse axis of symmetry and said connecting holes (144, 145, 146, 147, 148) are made in the middle (146, 147, 148) and on the ends (144, 145) of each plate (127a); moreover, each said plate is provided with two pairs of through mounting longitudinal slots (149, 150, 151, 152) made at the angle of 35–40° on both sides from the transverse axis of symmetry of the plate, and one of said vertebral fixation elements (109–126) made as half pin is secured in one mounting longitudinal slot of each pair, whereas the outer support units (1, 3) are connected with the intermediate one (2) with the help of connecting hinge junctions (174, 175, 176, 177, 178, 179), each of them being assembled from interconnected posts and each said post being provided with distraction rods (162, 163, 164, 165, 166, 167, 168, 169, 170, 171, 172, 173).

7. A device as claimed in claim 6, characterized that each of said connecting hinge junctions (174, 175, 176, 177, 178, 179) made as a ball head (189) set into a hollow sphere (192), both having cylindrical bulges (190, 194) with holes, said ball head is set from the truncated side of said hollow sphere having the inner surface covered with antifriction coating, while in the holes of said cylindrical bulges (190, 194) said distraction rods (162–173) are set, the truncated part (193) of said hollow sphere (192) is equal its ⅓, and the projection angle of the truncated part is 90°; moreover said ball head (189) is provided with recesses (196) and said hollow sphere (192) is provided with a hole (197) the axis of which is perpendicular to the axis of the holes of said cylindrical bulges (190, 194) and in which a lock (198) is set.

8. A technique of placement and management of the device for external transpedicular fixation of the spine, comprising percutaneous insertion of vertebral fixation elements (109–126) into the vertebral bodies, said elements being secured to fixation junctions (46, 47, 48, 49, 62, 63, 76, 77, 78) with subsequent application of distraction forces to the area of the spine involvement, characterized that a laminectomy and then discotomy of the spinal discs (239, 240) of cranial and caudal location being at the deformity apex are performed, autografts (241, 242, 243, 244) are inserted into the cavity of each disc and intact vertebrae ($Th_8$, $Th_7$, $Th_6$, $Th_{10}$, $Th_{11}$, $Th_{12}$, $L_2$, $L_3$, $L_4$) located above and below vertebral fixation elements (109–126) which are inserted into the centre of the pedicles of each arch at the angle of 30–45° to the sagittal plane passing through the axis of each vertebra, followed by graduated transport of said support units (1, 2, 3) and correspondingly of intact vertebrae ($Th_8$, $Th_7$, $Th_6$, $Th_{10}$, $Th_{11}$, $Th_{12}$, $L_2$, $L_3$, $L_4$) located above and below the area of surgery using said distraction threaded rods (4, 5, 6, 7, 8, 9), thus the spine is corrected to biomechanically normal position.

9. A device for external transpedicular fixation of the spine, comprising:
three support units (1,2,3), two of them being outer and one intermediate;
not more than six threaded rods (4, 5, 6, 7, 8, 9), connected so that may provide mutual spatial transport and indirect action on the intact vertebrae ($Th_8$, $Th_7$, $Th_6$ $Th_{10}$, $Th_{11}$, $Th_{12}$, $L_2$, $L_3$, $L_4$);
said two outer and one intermediate supports (1,2,3) comprise:
not more than nine fixation junctions (46, 47, 48, 49, 62, 63, 76, 77, 78) fastened into three groups with threaded ties (50, 51, 52, 64, 65, 66, 79, 80, 81) and each said fixation junction is made as a figure plate (127) having a transverse axis of symmetry (128) and provided with symmetric through longitudinal slots (129,130) located between the central bulge (131) and the ends shaped as a prism (132, 133) whereas
said central bulge (131) and said prism-shaped ends have connection holes (134, 135, 136) and fastening elements;
not more than two elements of vertebral fixation (109–126) are fastened with clamps (91–101) on each said figure plate;
each said element of vertebral fixation (109–126) is embodied as a half pin (screw pin) including:
a working end (180) which is cone, screw threaded, limited with a stopper (181) being olive-shaped;
a fastening end (189) having a flattening with a through hole (184), the axis of said hole being perpendicular to the longitudinal axis of said half pin.

10. The device as claimed in claim 9, wherein each of said half pins (109–126) is provided with a longitudinal slot (185) made all over the half pin length in which an injection needle (186) is fixed, and a cannula (187) provided with a plug (188) is set on said needle from the side of the fastening end (182) of said half pin.

11. The device as in claim 9, wherein each of said clamps (91–108) is embodied as an angular post including a cylinder with threaded surface (224) connected at an angle with a prismatic head (225) on the inner surface of which a cylindrical deepening (226) is done from the side of the threaded surface of the cylinder (224) and said threaded surface of the cylinder (224) is supplied with
conical (214) and spherical (215) washers.

12. The device as in claim 9, wherein each of said fixation junction (46, 47, 48, 49, 62, 63, 76, 77, 78) is embodied as a plate having a shape of an isosceles trapezium (127a) with a respectively transverse axis of symmetry and said plate comprises:
symmetrical through connecting holes (144, 145, 146, 147, 148), so that the axis of each of said connecting holes is perpendicular to the transverse axis of symmetry (143) and said connecting holes (144, 145, 146, 147, 148) are made in the middle and in the ends of each plate; moreover,
each said plate is provided with two pairs of through longitudinal mounting slots (149, 150, 151, 152) made at the angle of 35–40° on both sides from the transverse axis of symmetry of the plate, and one of said elements of vertebral fixation (109–126) made as a half pin is secured in one longitudinal mounting slot of each pair;

said outer support units (1, 3) are connected with the intermediate one (2) with the help of connecting hinge junctions (174, 175, 176, 177, 178, 179) including: interconnected posts and each said post is provided with a distraction rod (162–173).

13. The device as in claim 12, wherein a microschweller (204) is used having a closed longitudinal slot (219) on one of its planes and not less than two through mounting holes (220, 221) in each end of said microschweller plane (204) which is connected to said intermediate support unit (2) by means of two posts (211, 212) and threaded rods (205, 206) and through a connecting post having a lug and a threaded shank thus providing transportation in the sagittal plane together with said intermediate support unit (2).

14. A device as claimed in claim 12, wherein each of said connecting hinge junctions (174–179) comprises:
- a ball head (189) having recesses and a cylindrical bulge (190) with a hole
- a hollow sphere (192) having a cylindrical bulge (194) with a hole, a truncated part equal to ⅓ of said hollow sphere volume and located on the opposite side from its cylindrical bulge (194), moreover, the angle of said truncated part in projection is equal to 90 degrees whereas the inner surface of said hollow sphere is covered with antifriction coating;
- a lock (198), set into the hole (197) of said hollow sphere and perpendicular to the axes of the holes of the said cylindrical bulges (190, 194)
- distraction rods (162–173) mounted into the holes of said cylindrical bulges (190, 194).

15. The device as in claim 14, wherein said connecting hinge junction is embodied as a distraction rod (199) having a ball head on one end and said ball head is put into a sleeve (200) connected with a pivot (201) which is made on the end of the second distraction rod (202).

16. A technique for application and usage of the device of external transpedicular fixation of the spine, including:

percutaneous insertion of said elements of vertebral fixation (109–126) into vertebral bodies;

fastening of said elements of vertebral fixation to said fixation junctions (46, 47, 48, 49, 62, 63, 76, 77, 78)

subsequent application of distraction forces to the area of the spine involvement performance of a laminectomy and discotomy in the cranially and caudally located vertebral discs at the apex of the deformity;

introduction of autografts (241, 242, 243, 244) into the cavity of each disc (239, 240);

fixation of the intact vertebrae ($Th_6$, $Th_7$, $Th_8$, $Th_{10}$, $Th_{11}$, $Th_{12}$, $L_2$, $L_3$, $L_4$) located above and below using said vertebral fixation elements (109–126) which are inserted into the center of the pedicles of each arch at the angle of 30–45° to the sagittal plane that passes through the axis of each vertebra, a graduated transport of said support units (1, 2, 3) and, correspondingly, an indirect graduated transport of the intact vertebrae ($Th_8$, $Th_7$, $Th_6$, $Th_{10}$, $Th_{11}$, $Th_{12}$, $L_2$, $L_3$, $L_4$) located above and below the area of surgery using said distraction threaded rods (4, 5, 6, 7, 8, 9) until the spine is corrected to a bio-mechanically normal position.

* * * * *